US005842978A

United States Patent [19]
Levy

[11] Patent Number: 5,842,978
[45] Date of Patent: Dec. 1, 1998

[54] SUPPLEMENTAL AUDIO VISUAL EMERGENCY REVIEWING APPARATUS AND METHOD

[76] Inventor: Itchak Levy, 4835 Hollywood Blvd., Hollywood, Fla. 33021

[21] Appl. No.: 751,891

[22] Filed: Nov. 18, 1996

[51] Int. Cl.$^6$ .................................................. A61B 5/10
[52] U.S. Cl. ......................... 600/300; 600/508; 600/509; 600/524
[58] Field of Search ................................... 600/300, 508, 600/509, 523, 524, 525

[56] References Cited

U.S. PATENT DOCUMENTS

| | | | |
|---|---|---|---|
| 4,191,962 | 3/1980 | Sramek | 346/110 R |
| 4,805,631 | 2/1989 | Roi du Maroc, II | 128/710 |
| 4,858,617 | 8/1989 | Sanders | 128/696 |
| 4,922,909 | 5/1990 | Little et al. | 600/300 |
| 5,016,642 | 5/1991 | Dukes et al. | 128/696 |
| 5,279,305 | 1/1994 | Zimmerman et al. | 128/731 |
| 5,417,222 | 5/1995 | Dempsey et al. | 128/696 |
| 5,462,051 | 10/1995 | Oka et al. | 128/630 |
| 5,482,050 | 1/1996 | Smokoff et al. | 128/710 |
| 5,511,553 | 4/1996 | Segalowitz | 128/696 |
| 5,513,645 | 5/1996 | Jacobson et al. | 128/710 |
| 5,583,566 | 12/1996 | Kanno et al. | 600/109 |

*Primary Examiner*—Michael Peffley
*Assistant Examiner*—Stephen Huang
*Attorney, Agent, or Firm*—Flanagan & Flanagan; John R. Flanagan; John K. Flanagan

[57] ABSTRACT

A supplemental emergency reviewing apparatus and method includes the operative steps of connecting a medical monitoring system to a patient and monitoring a selected function of the patient to provide a data output signal for producing alphanumeric data about the selected function and an alarm output signal in response to the selected function reaching an alarm condition, aiming a CCTV camera at the patient and recording an image thereof to provide a video output signal for producing a video picture of the patient while the selected function is being monitored, receiving and combining in a video interface device the data output signal and video output signal to provide a combined video and data output signal for producing the video record superimposed with the alphanumeric data, receiving and indexing in a VCR device the combined video and data output signal and alarm output signal to provide an indexed combined video and data output signal for producing the video record with superimposed data which can be indexed to any point of an alarm condition so that a user when reviewing the indexed combined video and data output signal can access any indexed point to only review the patient and alphanumeric data at the time of each alarm condition, and receiving in a video monitor the indexed combined video and data output signal and producing the video record with the superimposed alphanumeric data on the monitor.

26 Claims, 4 Drawing Sheets ure and method of the present invention overcomes the drawbacks of the prior art by producing an integrated dynamic audio visual medical record of a patient's medical condition and permitting a physician to quickly and easily access and review only selected portions of the dynamic medical record which relate to an emergency or alarm state of the patient's medical condition.

SUPPLEMENTAL AUDIO VISUAL EMERGENCY REVIEWING APPARATUS AND METHOD

BACKGROUND OF THE INVENTION

1. Field of the Invention

The present invention generally relates to medical monitoring systems used to monitor vital functions of patients and, more particularly, is concerned with a supplemental audio visual emergency reviewing apparatus and method which produces a dynamic audio visual medical record of a patient's medical condition and permits a physician to quickly and easily access and review only selected portions of the audio visual medical record.

2. Description of the Prior Art

There are many types of medical monitoring systems that are used to monitor vital functions of patients, for instance oxygen saturation, heart/pulse rate, blood pressure, sleep apnea and the like. Typically, these devices display data via a seven segment display, LEDs, tones or a built-in printer. Also, these devices are usually programmable, allowing the user to create an alarm window. For example, if a pulse rate is being monitored, high and low rates can be programmed into the device and an alarm will sound (or whatever signaling device being used would be triggered) whenever the pulse rate deviates beyond (above or below) the given limits.

Often doctors require the monitoring of a patient, utilizing one of the above devices for any of a number of medical conditions. Monitoring would consist of a graphic image, such as a video tape, as well as a physical record, such as sheets of paper, of the data output generated by the monitoring device. Heretofore, the doctor has typically had to look at the two separate pieces of information, the image on the video tape and the data on the sheets of paper and mentally combine them to come up with a reasonable conclusion about the patient's medical condition. The doctor has not been able to observe the state of the patient at the time the data caused the alarm to occur. Information on the patient's state or condition at the time alarm data is generated is important for the doctor to have in order to properly interpret the data. For instance, similar data and thus a resultant alarm might be generated by very different causes, such as the movement or coughing of the patient, the temporary disruption of power to the device, or the occurrence of an actual event.

One prior art system has been disclosed in U.S. Pat. No. 4,805,631, issued to Roi du Maroc, II., for displaying on four separate windows or parts of a display screen the following: (1) an image of the movements of a patient, such as during swimming, (2) a record of electrical signals generated by monitoring and recording the activity of a selected organ of the patient, such as an electrocardiogram of the patient's heart, (3) instantaneous numerical values of the heart rhythm, and (4) the date and hour of the recording. While constituting a step in the right direction, this prior art system still has serious drawbacks in that it requires the user to simultaneously observe images which are not fully integrated with one another by appearing on separate windows or parts of a display screen and so is lacking in simplicity and user-friendliness. Also, the user is required to review the entire record since there is no means by which the user can select for review only certain levels of heart activity.

Consequently, a need still exists for development of an enhanced way to monitor a patient's medical condition that will overcome the drawbacks of the prior approaches to monitoring without introducing any new drawbacks in their place.

SUMMARY OF THE INVENTION

The present invention provides a supplemental audio visual emergency reviewing apparatus and method designed to satisfy the aforementioned need. The emergency reviewing apparatus and method of the present invention overcomes the drawbacks of the prior art by producing an integrated dynamic audio visual medical record of a patient's medical condition and permitting a physician to quickly and easily access and review only selected portions of the dynamic medical record which relate to an emergency or alarm state of the patient's medical condition.

The emergency reviewing apparatus and method employs readily commercially-available off-the-self electronic components in a novel and unique arrangement which produces on the same audio video tape a continuous audio record and video image of a patient combined with and superimposed by alphanumeric data about the functions of the patient being monitored so that a user, such as a physician or other medical staff, will have for review an integrated dynamic audio visual record of the patient's medical condition and will be able to access and review only those portions of the dynamic record that are relevant to alarm points in the patient's medical condition. The emergency reviewing apparatus and method is highly user-friendly by being relatively simple and straightforward to operate and use and employs a commercial video recording and replaying (VCR) device capable of being operated to index selected levels of activity of the patient for later selection for review. The record can be reviewed on a real-time basis and/or recorded on the video tape by the VCR device for later review on any VCR device. During the review, the user can "fast forward" the video tape to any indexed point and review only the events necessary. This saves time for the physician that would otherwise be wasted in having to review the entire tape. The physician can immediately observe the state of the patient, such as the position and/or activity of the patient, at the time of each alarm.

Accordingly, the present invention is directed to a supplemental emergency reviewing apparatus which comprises: (a) means for monitoring a selected function of a patient to provide a data output signal for producing data representative of the selected function in response to the selected function; (b) means for recording an image of the patient to provide a video output signal for producing a video record representative of the patient while the patient's selected function is being monitored; (c) means for receiving and combining the data output signal from the monitoring means and the video output signal from the recording means to provide a combined video and data output signal for producing the video record with the data superimposed thereon; and (d) means for receiving the combined video and data output signal from the combining means and producing the video record with the superimposed data.

The emergency reviewing apparatus also includes means for recording sounds made by the patient during monitoring to provide an audio signal for producing an audio record with the video record. The emergency reviewing apparatus further comprises means for receiving the audio signal and combined video and data output signal and the alarm output signal and indexing the latter signals to provide an audio output signal and an indexed video and data output signal for producing an audio record accompanying an indexed video record with the superimposed data which can be indexed to any point of an alarm condition reached by the monitored function as reflected by the data so that a user when reviewing the indexed record can access any indexed point to only produce and review the patient and data at the time of each alarm condition. The producing means then receives the audio output signal and indexed video and data output signal from the receiving and indexing means and produces the video record with the superimposed data and accompanying audio record at the time of each alarm condition.

The present invention also is directed to a supplemental emergency reviewing method which comprises the steps of: (a) monitoring a selected function of a patient to provide a data output signal for producing data representative of the selected function in response to the selected function; (b) recording an image of the patient to provide a video output signal for producing a video record representative of the patient while the patient's selected function is being monitored; (c) receiving and combining the data output signal and video output signal to provide a combined video and data output signal for producing a video record with the data superimposed thereon; and (d) receiving the combined video and data output signal and producing the video record with superimposed data. The emergency reviewing apparatus also includes the step of recording sounds made by the patient during monitoring to provide an audio signal along with the combined video and data output signal. The emergency reviewing method further comprises the steps of receiving the audio signal along with the combined video and data output signal and an alarm output signal and indexing the combined video and data output signal and the alarm output signal to provide an indexed video and data output signal for producing an audio record accompanying the video record with the superimposed data which can be indexed to any point of alarm so that a user when reviewing the indexed record can access any indexed point to only produce and review the patient and data at the time of each alarm.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
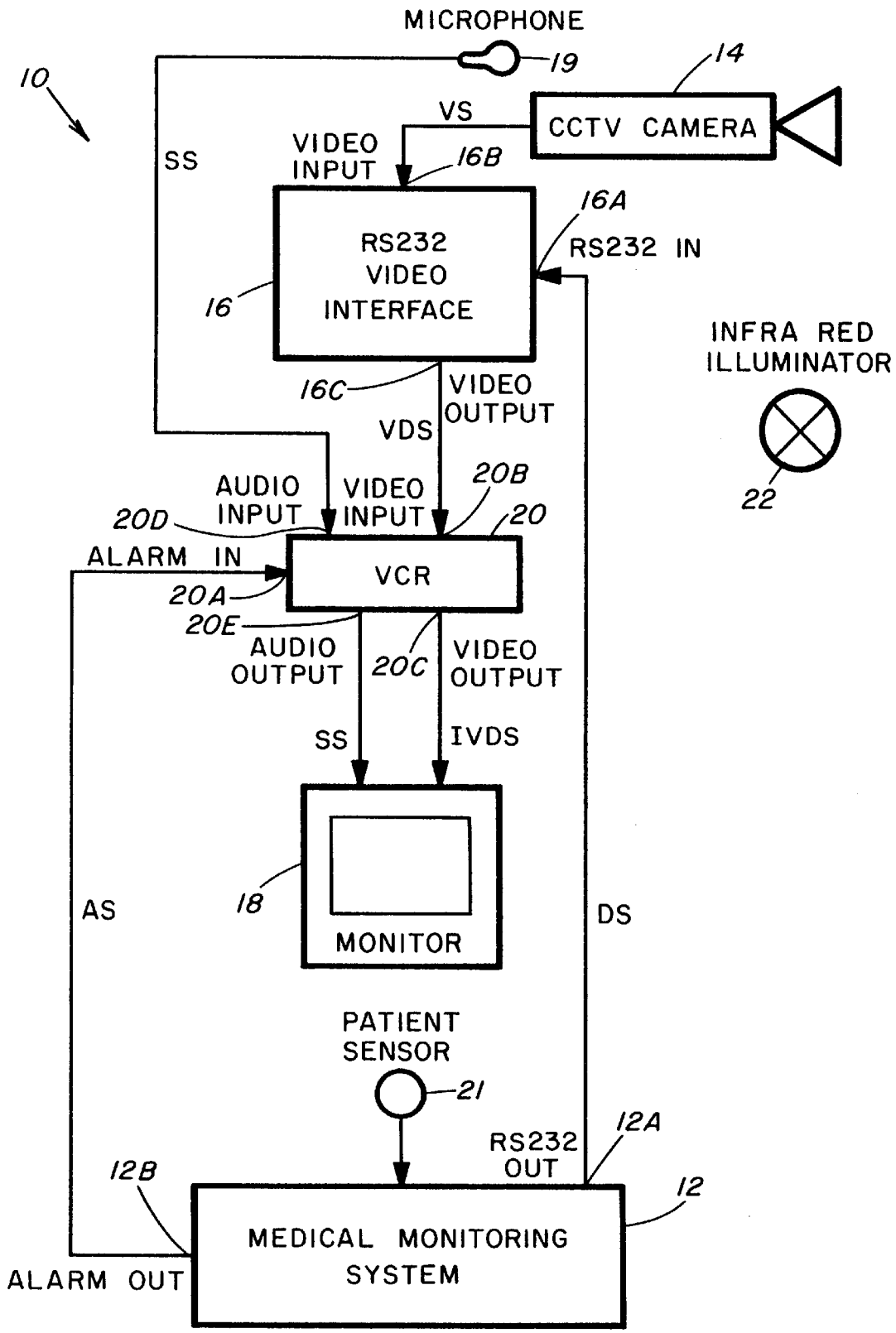
FIG. 1 is a block diagram of a preferred embodiment of a supplemental audio visual emergency reviewing apparatus of the present invention which operates in accordance with the method of the present invention.
Figure 2:
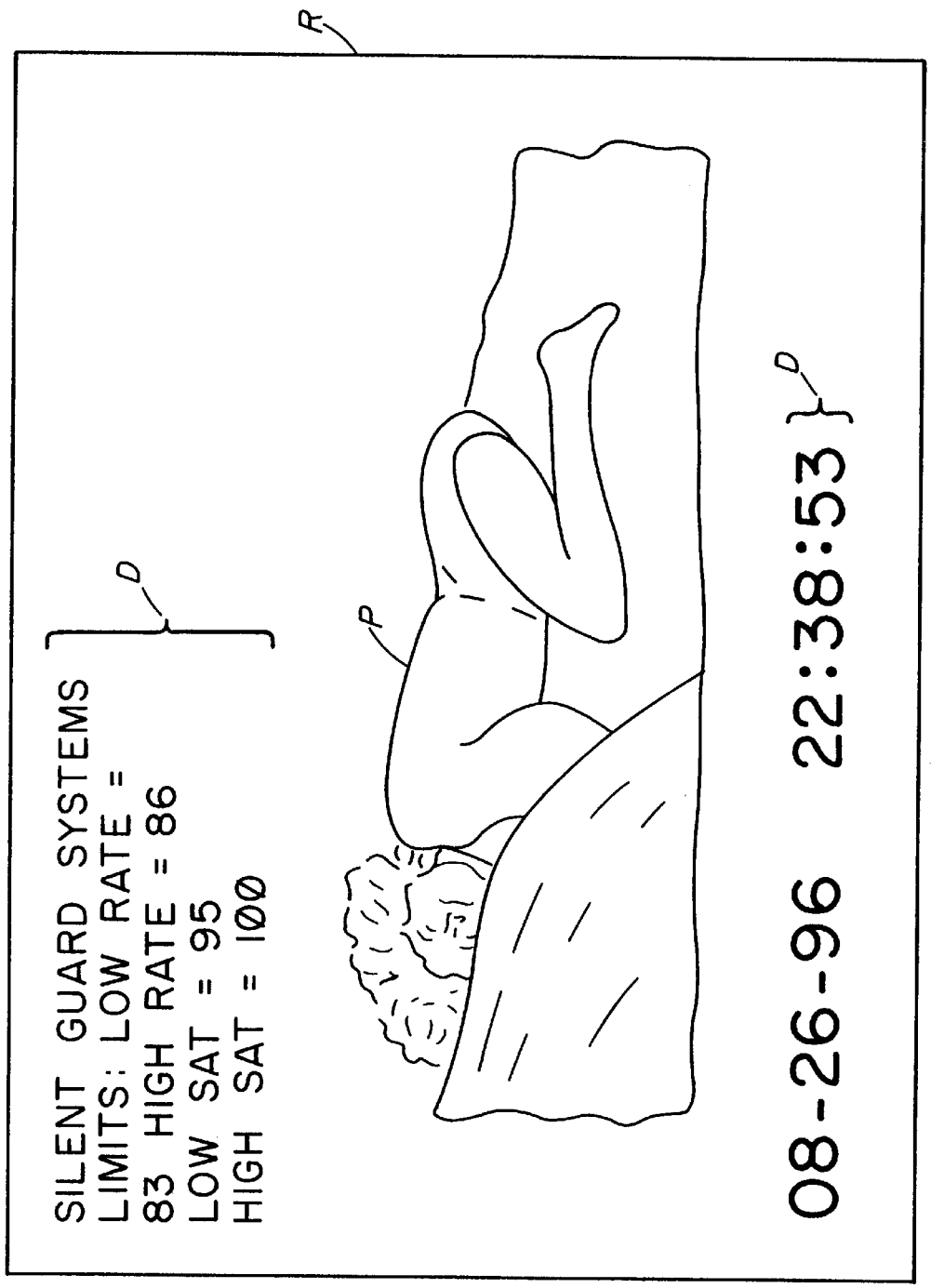
FIG. 2 is a representation of a video image of a patient with alphanumeric data superimposed thereon showing the position of the patient at the same time the data superimposed on the video image is indicating that the patient's condition is normal.
Figure 3:
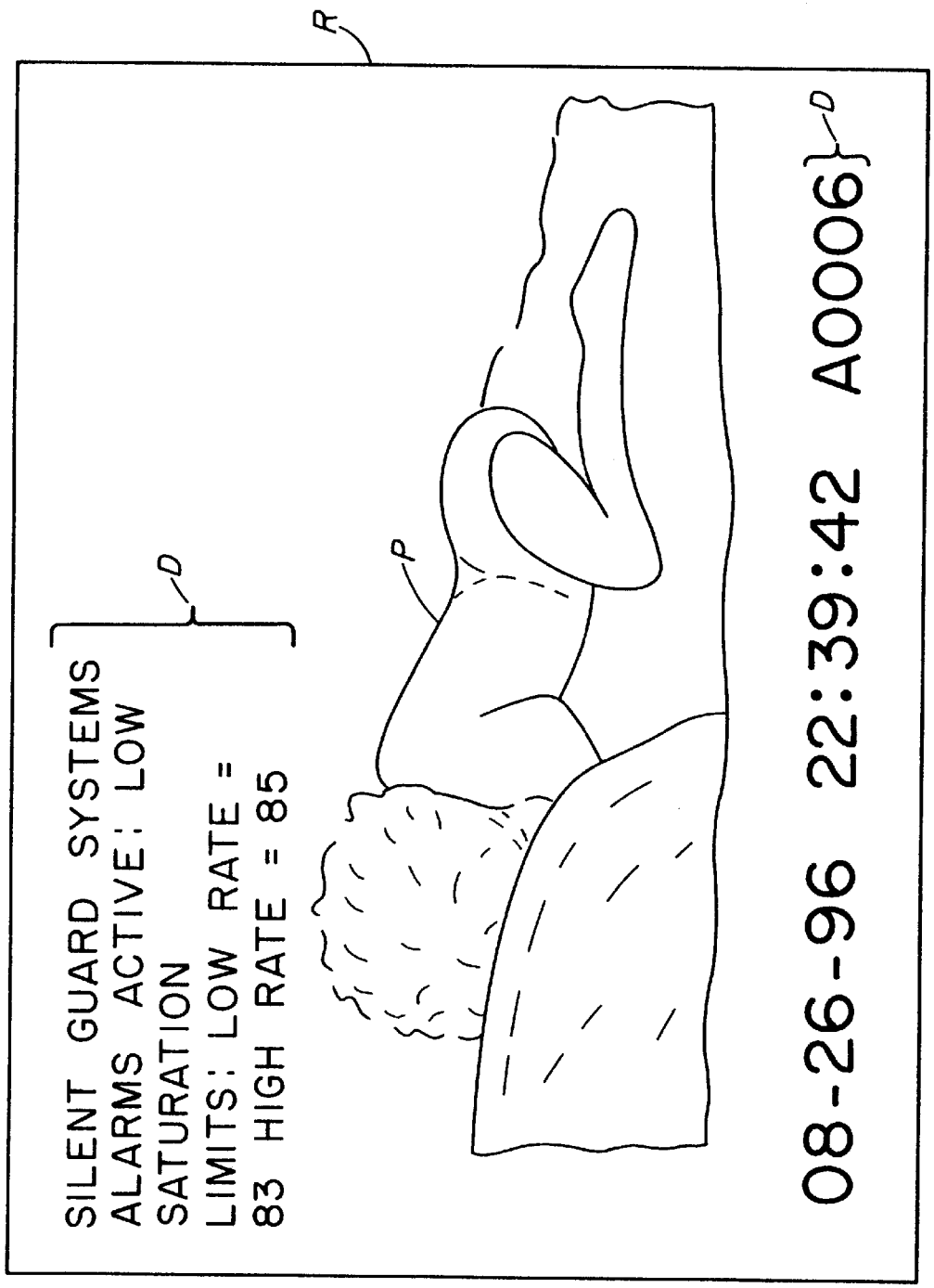
FIG. 3 is another representation similar to that of FIG. 2 but showing the position of the patient at the same time the data superimposed on the video image is indicating that the patient is in an alarm condition.

Referring to the drawings and particularly to FIG. 1, there is illustrated a supplemental audio visual emergency reviewing apparatus, generally designated 10, of the present invention. Basically, the emergency reviewing apparatus 10 includes means such as in the form of a medical monitoring system 12 for monitoring a selected function of a patient P, means such as in the form of a closed circuit television (CCTV) camera 14 for recording an image of the P patient during monitoring, means such as in the form of a video interface device 16 for receiving and combining signals, and means such as in the form of a video monitor 18 for receiving the combined signals and producing a video record of the patient for reviewing by a user. The apparatus 10 also includes means such as in the form of an audio pickup or microphone 19 for recording sounds made by the patient during monitoring to provide an audio signal for producing an audio record accompanying the video record, and means such as in the form of a recording and replaying (VCR) device 20 for receiving and indexing signals. As seen in FIGS. 2 and 3, the emergency reviewing apparatus 10 produces a continuous audio video record R with alphanumeric data D superimposed thereon providing information about the monitored functions. The video record with the superimposed data is indexed, by operation of the VCR device 20 in a known manner, to any point of an alarm condition of the data so that a user, such as a physician or other medical staff, when reviewing the video record R with the superimposed alphanumerica data D and accompanying audio record can access any indexed point to only review the patient and superimposed data at the time of occurrence of each alarm condition.

The medical monitoring system 12 of the apparatus 10 is of the type which monitors one or more selected functions, also known as vital signs or functions, of the patient P, such as oxygen saturation, heart/pulse rate, blood pressure, sleep apnea and the like. The medical monitoring system 12 has a serial RS232 communications output port 12A connected to a serial RS232 communications input port 16A of the video interface device 16 by which a data output signal DS produced by the system 12 is communicated to the video interface device 16 for producing alphanumeric data D representative of the selected function(s). The medical monitoring system 12 also has an alarm output port 12B connected to an alarm input port 20A of the VCR device 20 by which an alarm output signal AS provided by the system 12 is communicated to the VCR device 20. The alarm output signal AS is provided by the medical monitoring system 12 in response to the selected function(s) being monitored reaching an alarm condition, for example, by coming within preselected preset limits, such as high/low alarm settings on the system 12. The medical monitoring system 12 also has one or more sensor(s) 21 for connecting to the patient to monitor the selected function(s) of the patient and, in response thereto, to provide the data output signal DS representative of the selected function(s).

The closed circuit television (CCTV) camera 14 of the apparatus 10 is aimed at the patient so as to record continuously an image of the patient during the monitoring period and provide a video output signal VS on a commications line connected to a video input port 16B of the video interface device 16. The video output signal VS thus provided is used by the apparatus 10 for producing a continuous video record R, as seen in FIGS. 2 and 3, which shows the patient P while the patient's selected function(s) is being monitored by the medical monitoring system 12.

The video interface device 16 of the apparatus 10 receives the aforementioned data output signal DS from the medical monitoring system 12 and the video output signal VS from the CCTV camera 14 and combines the two and provides a combined video and data output signal VDS at its video output port 16C in which the alphanumeric data D is superimposed on the video record R. The video output 16C of the video interface device 16 is connected to a video input port 20B of the VCR device 20 for recording the combined video and data output signal VDS on a video tape. The video interface device 16 is also connected directly to the video monitor 18 so that the combined video and data output signal VDS can be reviewed on a real-time basis.

The microphone 19 is positioned near the patient P for sensing and recording any sounds made by the patient during the monitoring period. The microphone 19 may be a separate component as shown in FIG. 1 or built into the CCTV camera 14. The microphone 19 records the sounds and provides an audio or sound signal SS which is conducted to an audio input port 20D of the VCR device 20. The VCR device 20, in turn, supplies the audio output signal SS to the monitor 18 which produces the audio or sound record associated with the video record R and superimposed data D produced on the monitor. The audio or sound record assists the user in interpreting the data D superimposed on the video record R.

The VCR device 20 also receives and is programmed in a manner well-known to those skilled in the art to index the combined video and data output signal VDS received from the video interface device 16 with the alarm output signal AS received from the medical monitoring system 12 to provide an indexed combined video and data output signal IVDS for producing the video record R with the superimposed alphanumeric data D which can be indexed to any point of an alarm condition so that a user, such as a physician or other medical staff, when reviewing the indexed combined video and data output signal IVDS can access any indexed point to only review the video record R of the patient P and the superimposed alphanumerical data D with the accompanying audio record at the time of each alarm condition as seen in FIG. 3.

The video monitor 18, which can be a conventional television having audio and video inputs, receives the indexed combined video and data output signal IVDS from the video output port 20C of the VCR device 20 and the accompanying audio output signal SS from the audio output port 20E of the VCR device and produces an audio or sound record along with the video record R having the superimposed data D, as depicted in FIGS. 2 and 3. In FIG. 2, the data D superimposed on the video record R of the patient P indicates a normal (non-alarm) condition of the heart rate and oxygen saturation functions being monitored. The limits set are superimposed on the picture as low heart rate=83; high heart rate=86; low oxygen saturation=95; high oxygen saturation=100. Along the bottom portion of the video record R is generated the date and time.

In the event the system 12 monitoring the patient measures a number that exceeds the high/low alarm settings programmed on the system 12, the alarm output 12B of the system 12 will index the VCR device 20. In FIG. 3, the data D superimposed on the video record R of the patient P indicates an alarm condition exists due to the oxygen saturation rate being lower than the low limit programmed into the system 12. The date, time and index number are generated and superimposed by the VCR device 20 on the video record R. A user reviewing the video tape can do an index search and quickly find the location(s) on the video tape of the patient activity.

Referring to FIG. 1, the system 10 may also include the use of an infrared illuminator 22 for illuminating the patient with infrared energy to facilitate recording of the image by the CCTV camera 14 during periods of darkness. The infrared energy being invisible to the patient will not inadvertently disturb the patient and yet the sufficient light is provided for the CCTV camera 14 to produce a clear picture.

Figure 4:
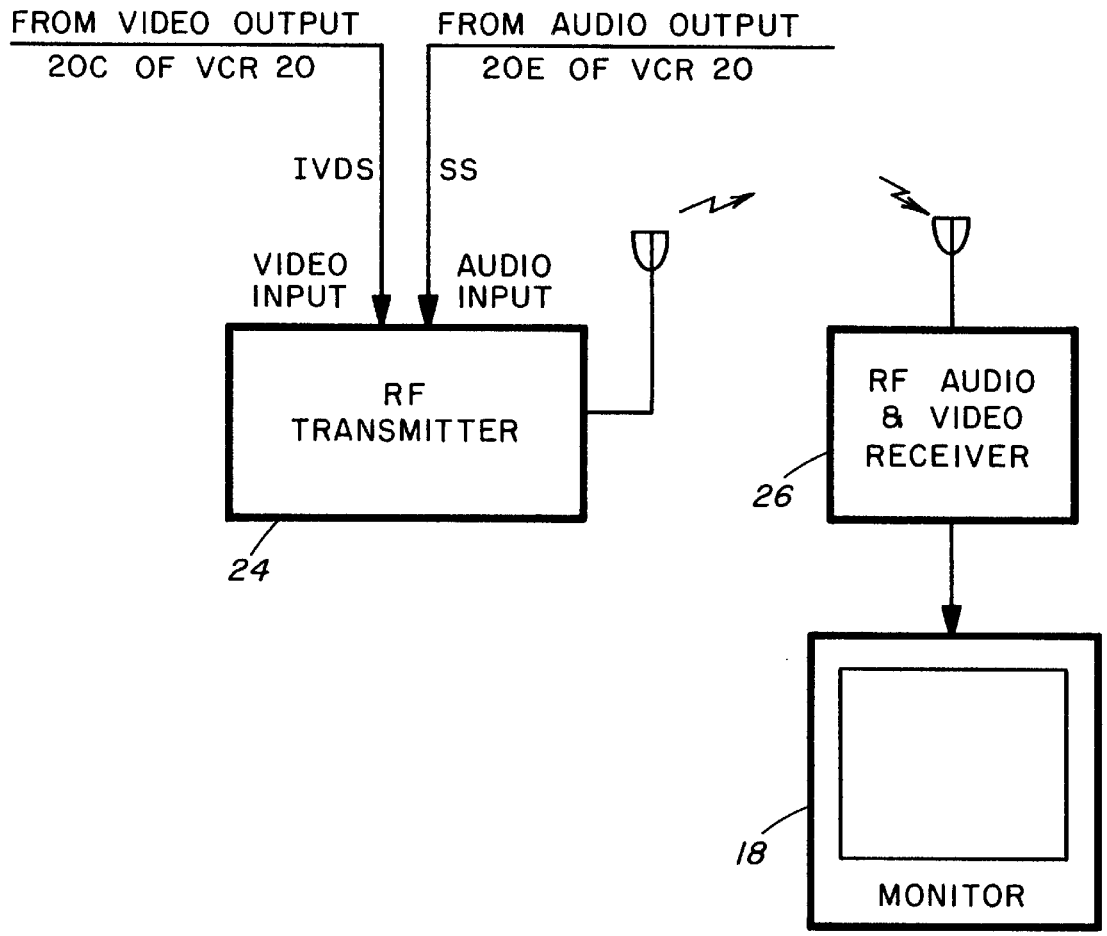
FIG. 4 is a block diagram of an optional wireless transmission modification for use by the apparatus of FIG. 1.

Referring to FIG. 4, the system 10 may also incorporate a RF transmitter 24 and a RF receiver 26. The RF transmitter 24 at a first location near to the patient receives the audio output signal SS and the indexed combined video and data output signal IVDS from the VCR device 20 and transmits the signals. The RF receiver 26 at a second location remote from the first location of the RF transmitter 24, such as in different buildings or only different rooms in the same building, receives the transmitted signals and inputs them to the video monitor 18, as described before, at the second location.

Given the above description of the supplemental audio visual emergency reviewing apparatus 10 of the present invention, it can now be readily understood how the apparatus 10 is capable of performing the method of the present invention which includes the following operative steps. First, the sensor 21 of the medical monitoring system 12 is connected to a patient and a selected function of the patient is monitored to produce a data output signal for providing alphanumeric data about the selected function and an alarm output signal in response to the selected function being within preselected limit or alarm range. Second, the CCTV camera 14 is aimed at the patient and records an image thereof to provide a video output signal for producing a video record of the patient and the microphone 19 is positioned near the patient and records and provides an audio signal for producing an audio record to accompany the video record while the selected function is being monitored. Third, the video interface device 16 receives and combines the data output signal and the video output signal to produce a combined video and data output signal in which the alphanumeric data is superimposed on the video picture. Fourth, the VCR device 18 receives the audio signal and provides an audio output signal and is operated to index the combined video and data output signal and alarm output signal to provide an indexed combined video and data output signal for producing an audio or sound record and an indexed video record having the superimposed alphanumeric data which can be indexed to any point of alarm so that a user, such as a physician, reviewing the indexed record can access any indexed point to only review the patient and superimposed alphanumeric data at the time of each alarm. Fifth and finally, the video monitor 18 receives the audio output signal and indexed combined video and data output signal and produces the audio or sound record and the video record superimposed with the alphanumeric data on the video monitor 18.

By way of example, one component which can be used to perform the functions of the medical monitoring system 12 is a pulse-oximeter manufactured by Nellcor and identified as model #N-200. One component which can be used to perform the functions of the video interface device 16 is a video serial interface manufactured by American Video Equipment and identified as model #VSI+. This interface device has an on-screen menu driven setup with programming options. There are so many readily-available components known to those of ordinary skill in this art that can be used to perform the functions of the CCTV camera 14, video monitor 18, microphone 19, and VCR device 20 that it is not necessary to cite any particular ones. It should be realized that the precise components making up an implementation of the apparatus 10 are not critical to the operation of the apparatus 10. It is only necessary that the components selected for the particular implementation provide the functions of the apparatus 10, which have been described above.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A supplemental emergency reviewing apparatus, comprising:

(a) means for monitoring a selected function of a patient to provide a data output signal for producing dynamic data representative of said selected function in response to said selected function;

(b) means for recording an external image of the patient concurrent with said monitoring of said selected function of the patient to provide a video output signal for producing a dynamic video record of any external movement made by the patient while the patient's selected function is being monitored;

(c) means for receiving and combining said data output signal from said monitoring means and said video output signal from said image recording means to provide a combined video and data output signal for producing said dynamic video record with said dynamic data superimposed thereon;

(d) means for recording sound made by the patient concurrent with said monitoring of said selected function and said recording of said external image of the patient to provide an audio signal representative of the sound made by the patient for producing a concurrent audio record accompanying said dynamic video record with said superimposed dynamic data; and (e) means for receiving said combined video and data output signal from said combining means and for receiving said audio signal from said sound recording means and producing said dynamic video record with said superimposed dynamic data and integrated with said concurrent audio record.

2. The apparatus of claim 1 wherein said monitoring means is a medical monitoring system having at least one sensor for connecting to the patient to monitor said selected function of the patient and provide said data output signal representative of said selected function.

3. The apparatus of claim 1 wherein said recording means is a closed circuit television camera for aiming at the patient to record said image of the patient and provide said video output signal.

4. The apparatus of claim 1 wherein said receiving and combining means is a video interface device.

5. The apparatus of claim 1 wherein said receiving and producing means is a video monitor.

6. The apparatus of claim 5 further comprising:

a transmitter for receiving at and transmitting from a first location said combined video and data output signal; and a receiver for receiving said transmitted combined video and data output signal at a second location remote from said first location and inputting said combined video and data output signal to said video monitor.

7. A supplemental emergency reviewing apparatus, comprising:

(a) means for monitoring a selected function of a patient to provide a data output signal for producing data representative of said selected function in response to said selected function;

(b) means for recording an image of the patient to provide a video output signal for producing a video record representative of the patient while the patient's selected function is being monitored;

(c) means for receiving and combining said data output signal from said monitoring means and said video output signal from said recording means to provide a combined video and data output signal for producing said video record with said data superimposed thereon;

(d) means for receiving said combined video and data output signal from said combining means and producing said video record with said superimposed data; and (e) means for illuminating the patient with infrared energy to facilitate recording of the image by said recording means during periods of darkness.

8. A supplemental emergency reviewing apparatus, comprising:

(a) means for monitoring a selected function of a patient to provide a data output signal for producing dynamic data representative of said selected function and an alarm output signal in response to said selected function reaching a preselected alarm condition;

(b) means for recording an external image of the patient concurrent with said monitoring of said selected function of the patient to provide a video output signal for producing a dynamic video record of the any external movement made by the patient while the patient's selected function is being monitored;

(c) means for receiving and combining said data output signal from said monitoring means and said video output signal from said image recording means to provide a combined video and data output signal for producing said dynamic video record with said dynamic data superimposed thereon;

(d) means for receiving and indexing said combined video and data output signal from said receiving and combining means and said alarm output signal from said monitoring means to provide an indexed video and data output signal for producing said dynamic video record with said superimposed dynamic data which can be indexed to any point of alarm condition so that a user when reviewing said indexed video and data output signal can access any indexed point to only review said dynamic video record with said superimposed dynamic data of the patient at the point of each alarm condition;

(e) means for recording sound made by the patient concurrent with said monitoring of said selected function and said recording of said external image of the patient to provide an audio signal representative of the sound made by the patient for producing a concurrent audio record accompanying said dynamic video record with said superimposed dynamic data; and (f) means for receiving said indexed video and data output signal from said receiving and indexing means and for receiving said audio signal from said sound recording means and producing at least at the time of each alarm condition said dynamic video record with said superimposed dynamic data and integrated with said concurrent audio record.

9. The apparatus of claim 8 wherein said monitoring means is a medical monitoring system having at least one sensor for connecting to the patient to monitor said selected function of the patient and provide said data output signal representative of said selected function.

10. The apparatus of claim 8 wherein said recording means is a closed circuit television camera aiming at the patient to record said image of the patient and provide said video output signal.

11. The apparatus of claim 8 wherein said receiving and combining means is a video interface device.

12. The apparatus of claim 8 wherein said receiving and indexing means is a video recording and replaying device.

13. The apparatus of claim 8 wherein said receiving and displaying means is a video monitor.

14. The apparatus of claim 13 further comprising:

a transmitter receiving at and transmitting from a first location said combined video and data output signal; and a receiver receiving said transmitted combined video and data output signal at a second location remote from said first location and inputting said combined video and data output signal to said video monitor.

15. A supplemental emergency reviewing apparatus, comprising:

(a) means for monitoring a selected function of a patient to provide a data output signal for producing data representative of said selected function and an alarm output signal in response to said selected function reaching a preselected alarm condition;

(b) means for recording an image of the patient to provide a video output signal for producing a video record representative of the patient while the patient's selected function is being monitored;

(c) means for receiving and combining said data output signal from said monitoring means and said video output signal from said recording means to provide a combined video and data output signal for producing said video record with said data superimposed thereon;

(d) means for receiving and indexing said combined video and data output signal from said receiving and combining means and said alarm output signal from said monitoring means to provide an indexed video and data output signal for producing said video record with said superimposed data which can be indexed to any point of alarm condition so that a user when reviewing said indexed video and data output signal can access any indexed point to only review the patient and data at the time of each alarm condition;

(e) means for receiving said indexed video and data output signal from said receiving and indexing means and producing said video record with said superimposed data at least at the time of each alarm condition; and (f) means for illuminating the patient with infrared energy to facilitate recording of the image by said recording means during periods of darkness.

16. A supplemental audio visual emergency reviewing apparatus, comprising:

(a) a medical monitoring system for monitoring a selected function of a patient to provide a data output signal for producing dynamic alphanumeric data representative of said selected function and an alarm output signal in response to said selected function reaching a preselected alarm condition;

(b) a closed circuit television camera for aiming at the patient to record an external image of the patient concurrent with said monitoring of said selected function of the patient and to provide a video output signal for producing a dynamic video record of any external movement made by the patient while the patient's selected function is being monitored by said medical monitoring system;

(c) a video interface device receiving said data output signal from said medical monitoring system and said video output signal from said closed circuit television camera to provide a combined video and data output signal for producing said dynamic video record with said dynamic alphanumeric data superimposed thereon;

(d) an audio pickup for positioning near the patient to record sound made by the patient concurrent with said monitoring of said selected function and said recording of said external image of the patient and to provide an audio signal for producing a concurrent audio record accompanying said dynamic video record with said superimposed dynamic alphanumeric data;

(e) a video recording and replaying device receiving said audio signal and receiving and indexing said combined video and data output signal and said alarm output signal to provide an audio output signal accompanying an indexed combined video and data output signal for producing said audio record accompanying said indexed dynamic video record with said superimposed dynamic alphanumeric data which can be indexed to any point of an alarm condition so that a user when reviewing said indexed record can access any indexed point to only review said dynamic video record with said superimposed dynamic alphanumeric data of the patient at the point of each alarm condition; and (f) a video monitor receiving said audio output signal and indexed combined video and data output signal from said video recording and replaying device and producing said indexed dynamic video record with said superimposed dynamic alphanumeric data and integrated with said concurrent audio record.

17. The apparatus of claim 16 wherein said medical monitoring system has at least one sensor for connecting to the patient to monitor said selected function of the patient to thereby provide said data output signal representative of said selected function.

18. The apparatus of claim 16 further comprising:

an infrared illuminator for illuminating the patient with infrared energy to facilitate recording of the image by said closed circuit television camera during periods of darkness.

19. The apparatus of claim 16 further comprising:

a RF transmitter receiving at and transmitting from a first location said combined video and data output signal and said accompanying audio output signal; and a RF receiver receiving said signals at a second location remote from said first location and inputting said signals to said video monitor.

20. A supplemental emergency reviewing method, comprising the steps of:

(a) monitoring a selected function of a patient to provide a data output signal for producing dynamic data representative of said selected function in response to said selected function;

(b) recording an external image of the patient concurrent with said monitoring of said selected function of the patient to provide a video output signal for producing a dynamic video record of any external movement made by the patient while the patient's selected function is being monitored;

(c) receiving and combining said data output signal and said video output signal to provide a combined video and data output signal for producing said dynamic video record with said dynamic data superimposed thereon;

(d) recording sound made by the patient concurrent with said monitoring of said selected function and said recording of said external image of the patient to provide an audio signal for producing a concurrent audio record accompanying said dynamic video record with said superimposed dynamic data; and (e) receiving said combined video and data output signal and said audio signal and producing said dynamic video record with said superimposed dynamic data and integrated with said concurrent audio record.

21. The method of claim 20 further comprising the steps of:

receiving at and transmitting from a first location said combined video and data output signal; and receiving said transmitted combined video and data output signal at a second location remote from said first location and inputting said combined video and data output signal to a video monitor for producing said video record with superimposed data.

22. A supplemental emergency reviewing method, comprising the steps of:

(a) monitoring a selected function of a patient to provide a data output signal for producing data representative of said selected function in response to said selected function;

(b) recording an image of the patient to provide a video output signal for producing a video record representative of the patient while the patient's selected function is being monitored;

(c) receiving and combining said data output signal and said video output signal to provide a combined video and data output signal for producing said video record with said data superimposed thereon;

(d) receiving said combined video and data output signal and producing said video record with said superimposed data; and (e) illuminating the patient with infrared energy to facilitate recording of the image during periods of darkness.

23. A supplemental emergency reviewing method, comprising the steps of:

(a) monitoring a selected function of a patient to provide a data output signal for producing dynamic data representative of said selected function and an alarm output signal in response to said selected function reaching a preselected alarm condition;

(b) recording an external image of the patient concurrent with said monitoring of said selected function of the patient to provide a video output signal for producing a dynamic video record of any external movement made by the patient while the patient's selected function is being monitored;

(c) receiving and combining said data output signal and said video output signal to provide a combined video and data output signal for producing said dynamic video record with said dynamic data superimposed thereon;

(d) receiving and indexing said combined video and data output signal and said alarm output signal to provide an indexed video and data output signal for producing said dynamic video record with superimposed dynamic data which can be indexed to any point of an alarm condition so that a user when reviewing said indexed record can access any indexed point to only review said dynamic video record with said superimposed dynamic data of the patient at the time of each alarm condition;

(e) recording sound made by the patient concurrent with said monitoring of said selected function and said recording of said external image of the patient to provide an audio signal representative of the sound made by the patient for producing a concurrent audio record accompanying said dynamic video record with said superimposed dynamic data; and (f) receiving said indexed video and data output signal and said audio signal and producing at least at the time of each alarm condition said dynamic video record with said superimposed dynamic data and integrated with said concurrent audio record.

24. The method of claim 23 further comprising the steps of:

receiving at and transmitting from a first location said combined video and data output signal; and receiving said transmitted combined video and data output signal at a second location remote from said first location and inputting said combined video and data output signal to a video monitor for producing said video record with superimposed data.

25. A supplemental emergency reviewing method, comprising the steps of:

(a) monitoring a selected function of a patient to provide a data output signal for producing data representative of said selected function and an alarm output signal in response to said selected function reaching a preselected alarm condition;

(b) recording an image of the patient to provide a video output signal for producing a video record representative of the patient while the patient's selected function is being monitored;

(c) receiving and combining said data output signal and said video output signal to provide a combined video and data output signal for producing said video record with said data superimposed thereon;

(d) receiving and indexing said combined video and data output signal and said alarm output signal to provide an indexed video and data output signal for producing said video record with said superimposed data which can be indexed to any point of an alarm condition so that a user when reviewing said indexed record can access any indexed point to only review the patient and data at the point of each alarm condition;

(e) receiving said indexed video and data output signal and producing said video record with said superimposed data at least at the time of each alarm condition; and (f) illuminating the patient with infrared energy to facilitate recording of the image during periods of darkness.

26. A supplemental audio visual emergency reviewing method, comprising the steps of:

(a) connecting a medical monitoring system to a patient and monitoring a selected function of the patient to provide a data output signal for producing dynamic alphanumeric data about the selected function and an alarm output signal in response to the selected function reaching a preselected alarm condition;

(b) aiming a closed circuit television camera at the patient and recording an external image thereof to provide a dynamic video output signal for producing a dynamic video record of any external movement made by the patient while the selected function is being monitored;

(c) receiving and combining in a video interface device the data output signal and video output signal to produce a combined video and data output signal for producing said dynamic video record with said dynamic alphanumeric data superimposed thereon;

(d) positioning an audio pickup near the patient to record sound made by the patient concurrent with said monitoring of said selected function and said recording of said external image of the patient and to provide an audio signal for producing a concurrent audio record accompanying said dynamic video record with said superimposed dynamic alphanumeric data;

(e) receiving in a video recording and replaying device the audio signal and the combined video and data output signal and alarm output signal and indexing the signals to provide an audio output signal accompanying an indexed combined video and data output signal for producing the audio record accompanying the indexed dynamic video record with said superimposed dynamic alphanumeric data which can be indexed to any point of an alarm condition so that a user when reviewing the indexed record can access any indexed point to only review said dynamic video record with said superimposed dynamic alphanumeric data of the patient at the point of each alarm condition; and (f) receiving in a video monitor the audio output signal and indexed combined video and data output signal and producing said indexed dynamic video record with said superimposed dynamic alphanumeric data and integrated with said concurrent audio record.

* * * * *